US007457719B1

(12) United States Patent
Kahn et al.

(10) Patent No.: US 7,457,719 B1
(45) Date of Patent: Nov. 25, 2008

(54) ROTATIONAL INSENSITIVITY USING GRAVITY-BASED ADJUSTMENT

(75) Inventors: Philippe Kahn, Aptos, CA (US); Arthur Kinsolving, Santa Cruz, CA (US); Mark Andrew Christensen, Santa Cruz, CA (US); Brian Y Lee, Aptos, CA (US)

(73) Assignee: Fullpower Technologies, Inc., Santa Cruz, CA (US)

( * ) Notice: Subject to any disclaimer, the term of this patent is extended or adjusted under 35 U.S.C. 154(b) by 105 days.

(21) Appl. No.: 11/603,472

(22) Filed: Nov. 21, 2006

(51) Int. Cl.
*G01P 15/00* (2006.01)
(52) U.S. Cl. .................................................. 702/141
(58) Field of Classification Search ............... 702/141; 318/636; 725/37
See application file for complete search history.

(56) References Cited

U.S. PATENT DOCUMENTS

| 5,654,619 | A  | * | 8/1997 | Iwashita ..................... 318/636 |
| 6,532,419 | B1 |   | 3/2003 | Begin et al. |
| 6,885,971 | B2 |   | 4/2005 | Vock et al. |
| 6,928,382 | B2 | * | 8/2005 | Hong et al. .................. 702/141 |
| 2007/0130582 | A1 | * | 6/2007 | Chang et al. .................. 725/37 |

OTHER PUBLICATIONS

Dao, Ricardo, "Inclination Sensing with Thermal Accelerometers", MEMSIC, May 2002, 3 pages.
Lee, Seon-Woo and Kenji Mase, "Recognition of Walking Behaviors for Pedestrian Navigation", IEEE International Conference on Control Applications, 2001, http://ieeexplore.ieee.org/xpl/absprintf.jsp?arnumber=974027&page=FREE, 5 pages.
Mizell, David, "Using Gravity to Estimate Accelerometer Orientation", Seventh IEEE International Symposium on Wearable Computers, 2003, 2 pages.
Weinberg, Harvey, "MEMS Motion Sensors Boost Handset Reliability", Jun. 2006, http://www.mwrf.com/Articles/Print.cfm?ArticleID=12740, Feb. 21, 2007, 4 pages.

* cited by examiner

*Primary Examiner*—Tung S Lau
*Assistant Examiner*—Xiuquin Sun
(74) *Attorney, Agent, or Firm*—Blakely, Sokoloff, Taylor & Zafman, LLP; Judith A. Szepesi (57) ABSTRACT

One or more rolling averages of accelerations over a sample period are created. The one or more rolling averages of accelerations are measured by an accelerometer over the sample period. A gravitational influence is identified based upon the one or more rolling averages of accelerations. A dominant axis is assigned based upon the gravitational influence.

43 Claims, 9 Drawing Sheets

ROTATIONAL INSENSITIVITY USING GRAVITY-BASED ADJUSTMENT

FIELD OF THE INVENTION

This invention relates to a method of determining an orientation of an accelerometer and a device that exhibits a rotational insensitivity using a gravity-based adjustment.

BACKGROUND

The development of microelectromechanical systems (MEMS) technology has enabled manufacturers to produce accelerometers sufficiently small to fit into portable electronic devices. Such accelerometers can be found in a limited number of commercial electronic devices such as cellular phones, game controllers, and portable computers.

Generally, devices that utilize an accelerometer to measure motion to detect steps or other activities require the user to first position the device in a specific orientation. In some devices, the required orientation is dictated to the user by the device. In other devices, the beginning orientation is not critical, so long as this orientation can be maintained. However, it can be difficult to keep a portable device in a fixed orientation.

BRIEF DESCRIPTION OF THE DRAWINGS

The present invention is illustrated by way of example, and not by way of limitation, and can be more fully understood with reference to the following detailed description when considered in connection with the following figures.

DETAILED DESCRIPTION

Embodiments of the present invention are designed to identify a dominant axis of an accelerometer based on gravity. The dominant axis can facilitate the use of accelerometers for monitoring user activity. In one embodiment, a dominant axis is assigned after creating a rolling average of accelerations over a sample period and identifying a gravitational influence based upon the rolling average of accelerations.

Figure 1:
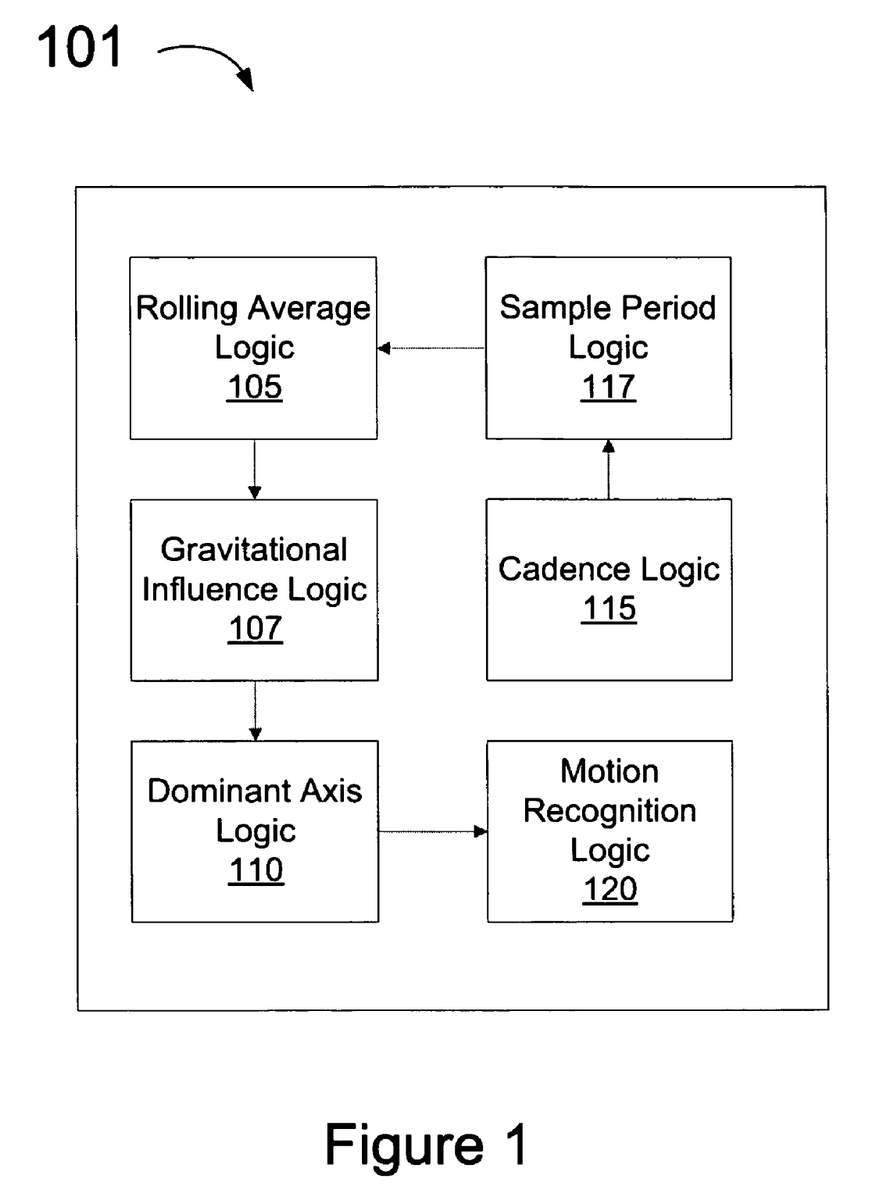
FIG. 1 is a block diagram illustrating one embodiment of an electronic device.

FIG. 1 is a block diagram illustrating an electronic device 101 in accordance with one embodiment of the present invention. The electronic device 101 comprises a rolling average logic 105, a gravitational influence logic 107, a dominant axis logic 110, a cadence logic 115, a sample period logic 117, and a motion recognition logic 120. In one embodiment, the electronic device 101 is a portable electronic device that includes an accelerometer.

The rolling average logic 105 creates one or more rolling averages of accelerations as measured by an accelerometer over a sample period. In one embodiment, the rolling average logic 105 creates a rolling average of accelerations along a single axis. In another embodiment, the rolling average logic 105 creates rolling averages of accelerations along multiple axes. The length of the sample period over which the rolling average is taken determines the amount of past acceleration data that is averaged with present acceleration data. In a longer sample period, more past acceleration data is stored.

The rolling average logic 105 can create a simple rolling average and/or an exponential rolling average. In a simple rolling average, all data is treated equally. In an exponential rolling average, the most recent data is given more weight. In one embodiment, the rolling average logic 105 creates a rolling average for each of the axes along which acceleration data is taken.

In one embodiment, the cadence logic 115 detects a period of a cadence of motion based upon user activity, and the sample period logic 117 sets the sample period of the rolling averages based on the period of the cadence of motion. In one embodiment the gravitational influence logic 107 identifies a gravitational influence based upon the rolling averages of accelerations. The dominant axis logic 110 assigns the dominant axis based upon the gravitational influence. The motion recognition logic 120 can use the dominant axis to facilitate motion recognition.

Figure 2A:
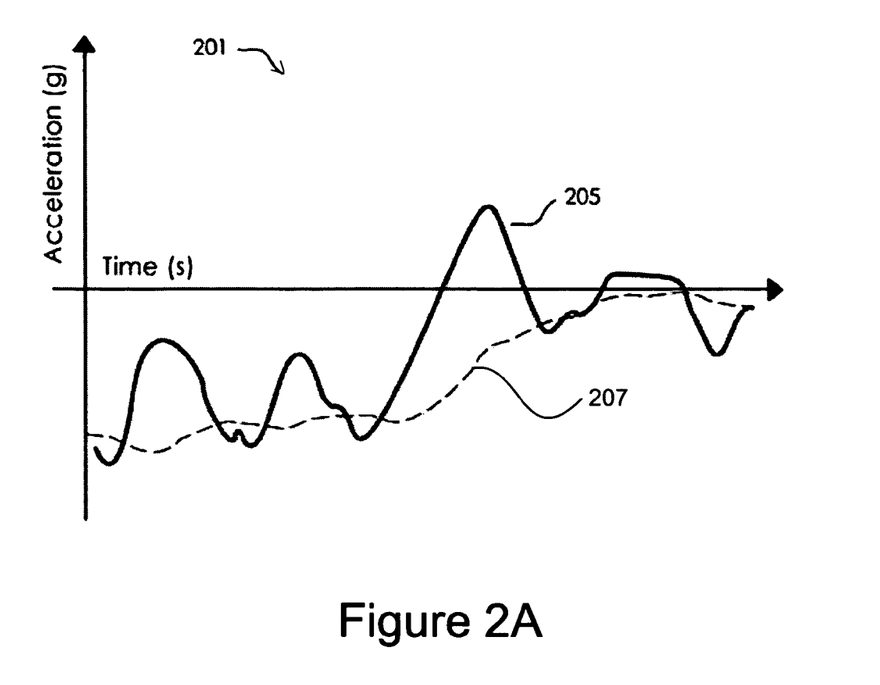
FIGS. 2A and 2B illustrate exemplary rolling average graphs that measure time versus acceleration.
Figure 2B:
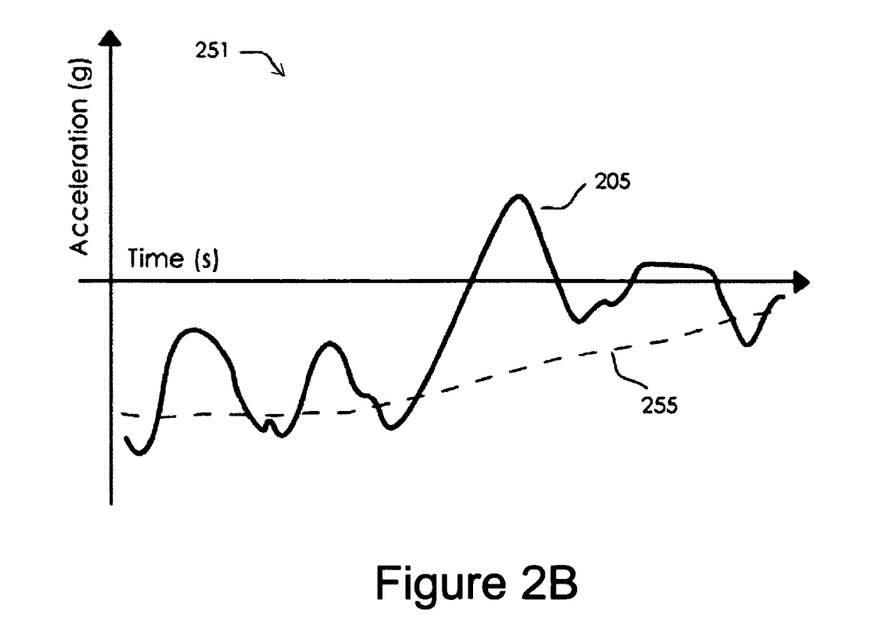

FIGS. 2A and 2B illustrate an exemplary first rolling average graph 201 and second rolling average graph 251, respectively. Both graphs represent time versus acceleration, shown by line 205. The first rolling average graph 201 shows a first rolling average 207 based on a relatively short sample period. The second rolling average graph 251 shows a second rolling average 255 based on a longer sample period. The length of the sample period determines how sensitive the rolling average is to fluctuations in acceleration. A short sample period as shown in FIG. 2B will measure brief fluctuations. In a longer sample period, as shown in FIG. 2A, brief fluctuations are averaged out. Additionally, a rolling average always lags behind the present acceleration, and a longer sample period causes greater lag. Comparing FIGS. 2A and 2B, it can be seen that the second rolling average 255 requires more time than the first rolling average 207 to reflect a change in acceleration.

In one embodiment, the sample period is preconfigured. In one embodiment, the size of the sample period is adjusted based on the application(s) using the accelerometer data. In one embodiment, the sample period can be user selected from a list of options. In one embodiment, the sample period can be determined by the cadence logic 105 and the sample period logic 118.

In one embodiment, two or more rolling averages of accelerations are tracked concurrently. The two or more rolling averages can be rolling averages along the same or different axes. In one embodiment, two or more rolling averages are tracked concurrently for each of the axes. Concurrent tracking of rolling averages can be beneficial where a user is performing two actions at the same time, each of which requires a different level of sensitivity for acceleration measurements. For example, the use of different sample periods for two rolling averages can be useful where the electronic device 101 is simultaneously counting steps and tracking motions of a user as called for by a motion sensitive game. In such an example, the motion sensitive game might require a very short sample period to measure quick motions, while the step counter might require a longer sample period so as to register only the user's steps.

Returning to FIG. 1, in one embodiment the cadence logic 115 detects a period of a cadence of motion based upon user activity (e.g. rollerblading, biking, running, walking, etc). Many types of motions that are useful to keep track of have a periodic set of movements. Specific periodic human motions may be characteristic of different types of user activity. For example, to walk, an individual must lift a first leg, move it forward, plant it, then repeat the same series of motions with a second leg. In contrast, a person rollerblading performs a repeated sequence of pushing, coasting, and lift-off for each leg. For a particular individual, the series of walking motions will usually occur in the same amount of time, and the series of rollerblading motions will usually occur in about the same amount of time. The repeated set of motions defines the cadence of the motion, while the amount of time over which the series of motions occurs defines the period of the cadence of the motion. For simplicity, the term "step" is used in this application to describe the user activity being evaluated. However, in the context of this application, the term "step" should be taken to mean any user activity having a periodic set of movements.

Figure 3:
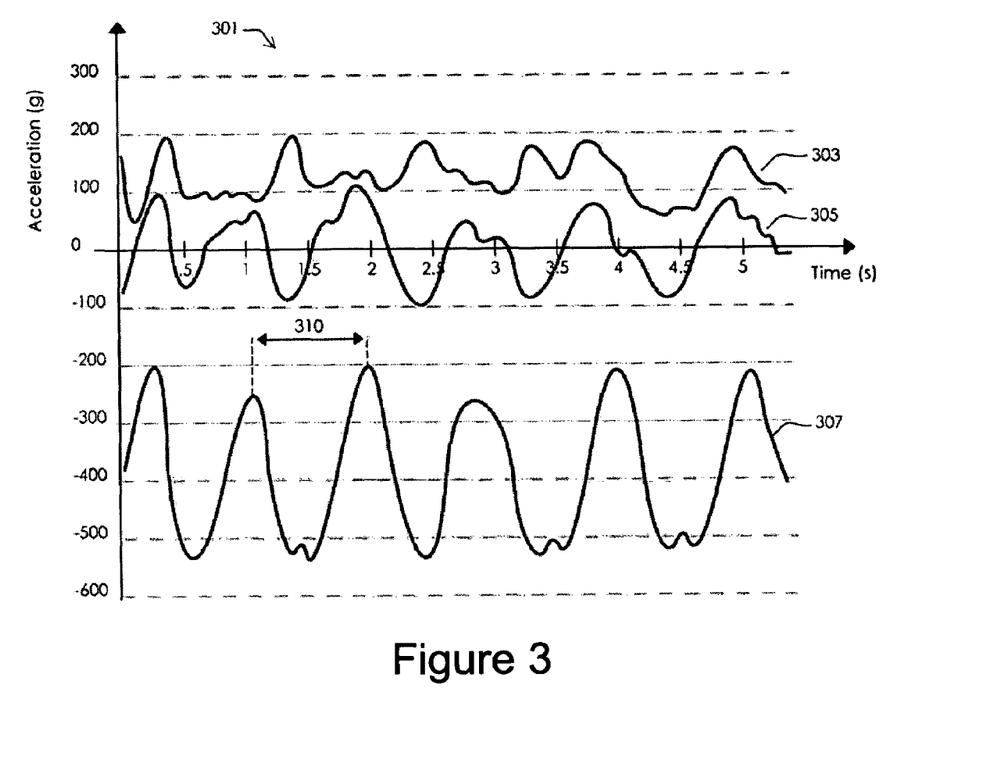
FIG. 3 illustrates an exemplary cadence of motion graph that measures time versus acceleration.

FIG. 3 illustrates a cadence of motion graph 301 that measures time versus acceleration. The acceleration at a given period of time is represented for a first axis 303, a second axis 305, and a third axis 307. In one embodiment, a cadence logic analyzes the acceleration along the first axis 303, second axis 305 and third axis 307 to detect a pattern. Once a pattern is detected, a period of the pattern is determined. This period corresponds to the period of the cadence of motion. FIG. 3 shows a period of a cadence of motion 310 for the third axis 307. The same period can also be seen to a lesser degree in the second axis 305 and the first axis 303.

In one embodiment, periods can be determined for multiple cadences of motion. For example, if a user simultaneously walks and tosses a ball in the air, in one embodiment the system can detect a period of the cadence of tossing the ball, and a period of the cadence of walking.

Returning back to FIG. 1, once the period of a cadence of motion is detected, the sample period logic 117 can set the sample period of the rolling average based upon the period of the cadence of motion. In one embodiment, the sample period is set such that it is approximately the length of the period of the cadence of motion. Alternatively, the sample period can be set so that it exceeds the length of the period of the cadence of motion. In one embodiment, the sample period is set such that it is a multiple of the period of the cadence of motion.

In one embodiment, the gravitational influence logic 107 identifies a gravitational influence based upon the rolling average or averages of accelerations. An accelerometer measures both dynamic accelerations, caused by user movement, and static acceleration, caused by gravity. This static acceleration is measured by an accelerometer as a constant acceleration that is equal and opposite to the force of gravity. Over a period of a cadence of motion, the dynamic acceleration caused by user activity tends to average towards zero, which leaves primarily the static acceleration. The axis with the largest absolute rolling average is the axis most influenced by gravity.

The axis that is most influenced by gravity can change over time. For example, as an electronic device 101 is rotated, the influence of gravity will change for at least two axes in a three axis accelerometer. At some point in the rotation, the axis that experiences the most gravitational influence will change. This change is shown in FIGS. 4A and 4B.

Figure 4A:
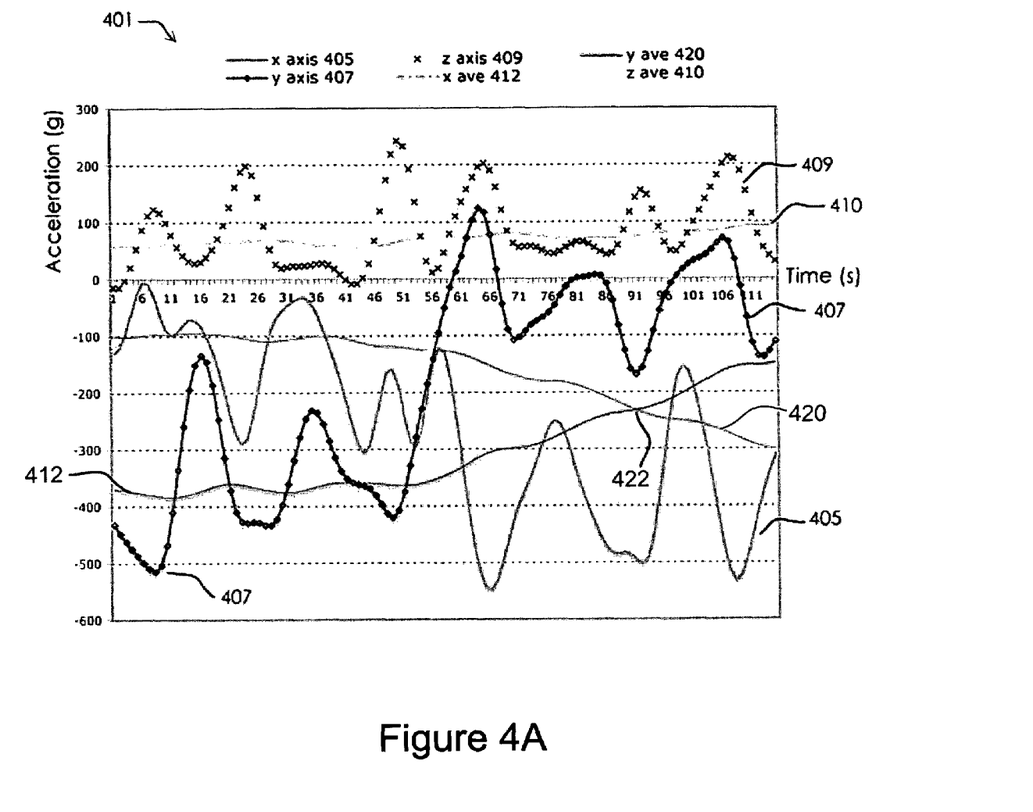
FIGS. 4A and 4B illustrate exemplary gravitational influence graphs.

FIG. 4A illustrates a first gravitational influence graph 401 for a data set over a rolling average sample period of 2.5 seconds. Accelerations are shown along an x-axis 405, a y-axis 407, and a z-axis 409. In FIG. 4A, a device being measured is rotated about the z axis over time. At time T=0, the y-axis 407 has the largest absolute acceleration value at over −400, while at time T=111 the x-axis has the largest absolute acceleration value at −300.

In FIG. 4A, a first x-axis rolling average 412, a first y-axis rolling average 420 and a first z-axis rolling average 410 are shown. The axis with the largest absolute rolling average is the axis that is most influenced by gravity at a given time. As rotation occurs, the rolling averages change to reflect a change in the gravitational influence on the device. Initially, the x-axis 405 is most influenced by gravity. At the first point of intersection 422 of the first x-axis rolling average 412 and the first y-axis rolling average 420, the y-axis 407 becomes the axis most influenced by gravity. However, the axis that experiences the greatest gravitational influence changes at a time after the rotation has actually occurred. This is due to a lag caused by the 2.5 second sample period. To reduce this lag, the sample period can be reduced.

Figure 4B:
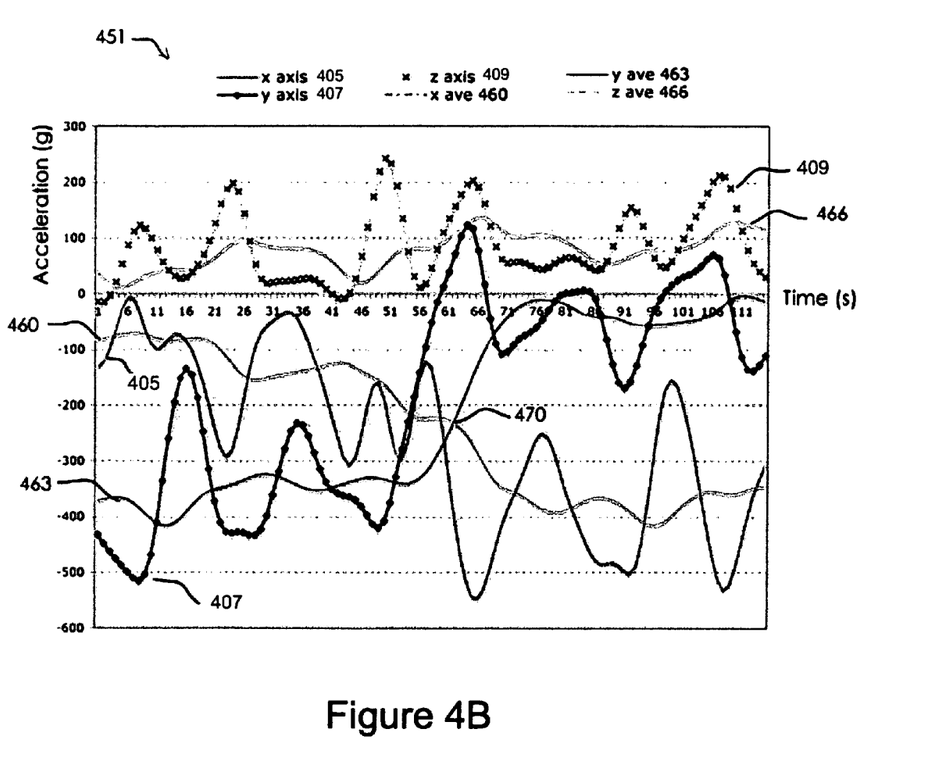

FIG. 4B illustrates a second gravitational influence graph 451 for the same data set as shown in FIG. 4A over a rolling average sample period of 1 second. FIG. 4B shows a second x-axis rolling average 460, a second y-axis rolling average 463 and a second z-axis rolling average 466. As shown, a second point of intersection 470 occurs between the second x-axis rolling average 460 and second y-axis rolling average 463 much earlier in time than the first point of intersection 422. The earlier point of intersection more accurately reflects the time when rotation actually occurs. As shown by FIGS. 4A and 4B, a change in the length of the sample period for the rolling average can greatly affect the sensitivity of the device to changes in orientation.

In one embodiment, the gravitational influence logic 107 calculates the total gravity caused acceleration based upon the acceleration on each axis. The gravitational influence logic 107 in one embodiment then assigns a percentage of the total acceleration to each axis. From the percentage of total acceleration on the axes the gravitational influence logic 107 then calculates the approximate device orientation.

Referring back to FIG. 1, the dominant axis logic 110 assigns a dominant axis based upon the gravitational influence. In one embodiment, the actual axis with the largest absolute rolling average over the sample period is assigned as the dominant axis. In this embodiment, the dominant axis therefore corresponds to the axis having the largest absolute rolling average at a given time. In an alternative embodiment, the dominant axis does not correspond to one of the actual axes of the accelerometer in its current orientation, but rather to an axis that is defined as aligned to gravity.

Figure 5:
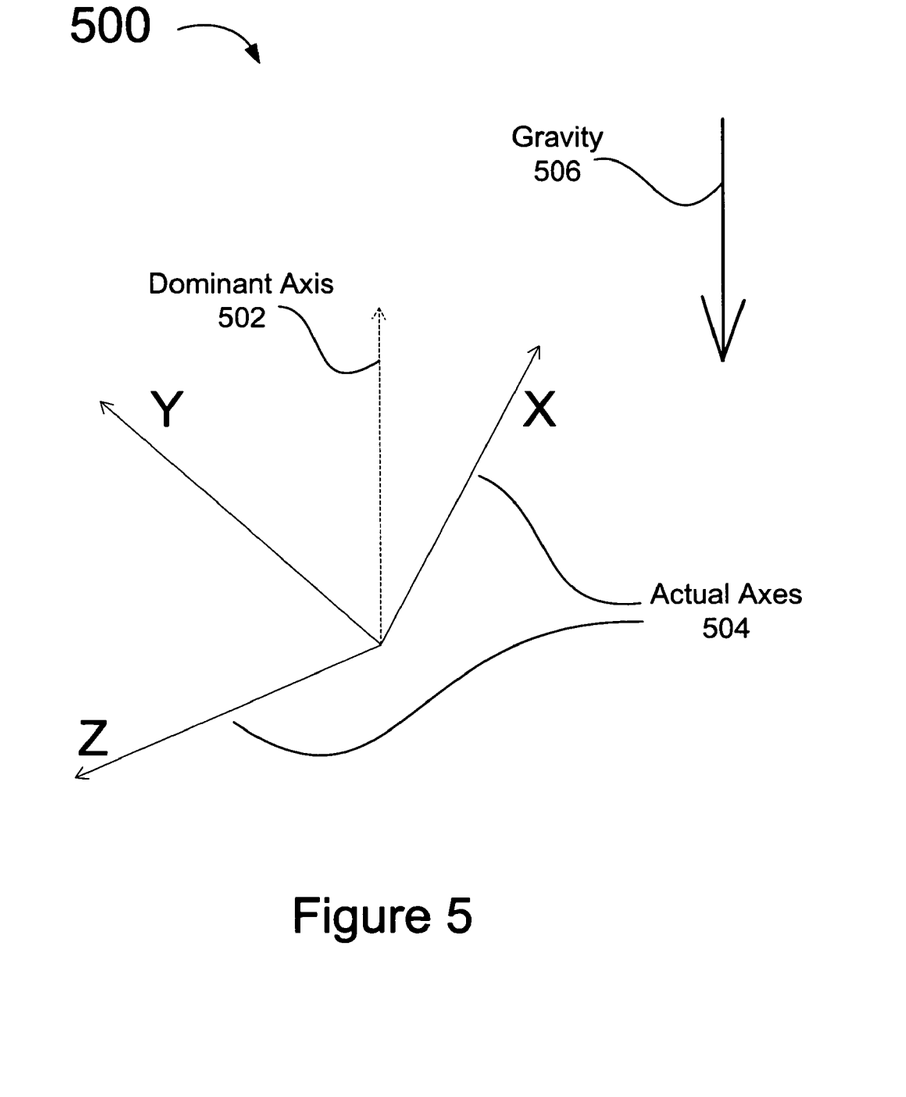
FIG. 5 illustrates a plan view of a dominant axis that does not correspond to an actual axis.

FIG. 5 illustrates a plan view 500 of an exemplary dominant axis 502 that does not correspond to one of the actual axes 504 of an accelerometer. The dominant axis 502, as shown in FIG. 5, can be a component of the x axis, y axis, and/or z axis, and is approximately aligned with gravity 506. In one embodiment, the dominant axis 502 corresponds to a virtual axis that is a component of a virtual coordinate system. The relationship between the virtual coordinate system and the actual coordinate system can be determined by performing a coordinate transformation. In one embodiment, the virtual coordinate system is a virtual Cartesian coordinate system, in which the dominant axis is one of a virtual x-axis, y-axis or z-axis. In alternative embodiments, the dominant axis 502 is a virtual axis of, for example, a polar coordinate system.

In one embodiment, the dominant axis logic 110 assigns the dominant axis by performing a true gravity assessment. A true gravity assessment may be performed by doing trigonometric calculations on the actual axes based on the gravitational influence. For example, the arcsine function can determine the exact angle between the actual axes and the gravitational influence. True gravity assessments can exactly align the dominant axis with the gravitational influence, but can be resource expensive.

In one embodiment, the dominant axis logic 110 assigns the dominant axis by comparing the gravitational influence to a lookup table. A lookup table provides greater accuracy than assigning the dominant axis to the axis that has the largest acceleration, and is less resource expensive than calculating the exact gravitational influence on each axis. A lookup table divides accelerations into known limits that define a probability range in which gravity is acting.

Figure 6:
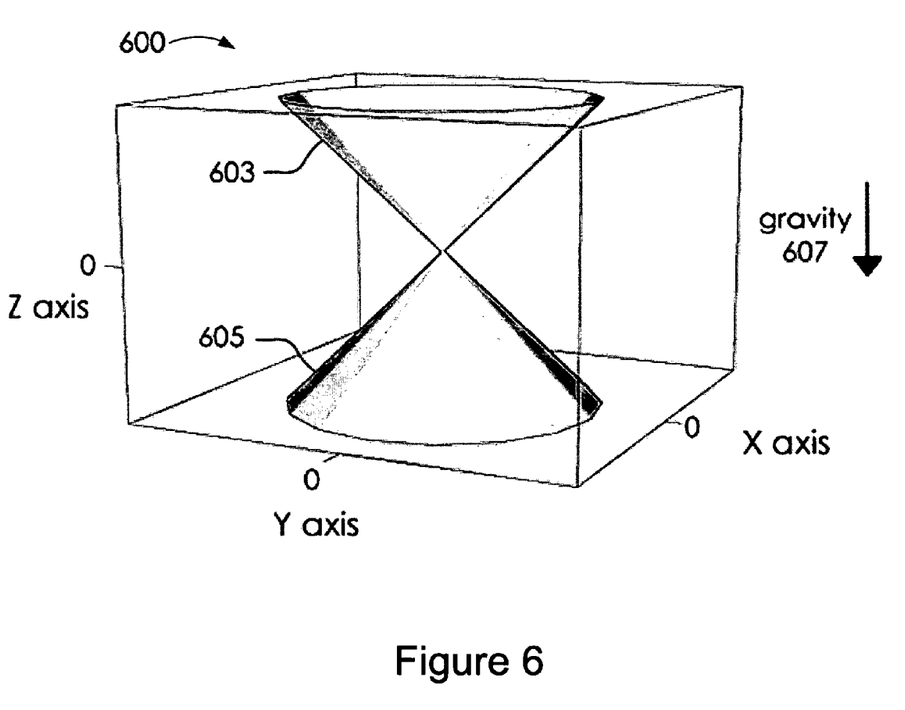
FIG. 6 illustrates an exemplary probability range represented by a plurality of cones.

FIG. 6 illustrates an exemplary probability range 600 represented by a plurality of projections, each of the projections corresponding to an entry on a lookup table. In the illustrated embodiment, the area of space swept by the projections defines a cone. In alternative embodiments, the area of space swept by the projections defines other shapes. The lookup table that corresponds to the exemplary probability range 600 has six entries, each of which corresponds to a projection having an included angle between opposite sides of ninety degrees. For example, if the gravitational influence acts within the first projection 603, then the table entry that corresponds to that projection is assigned as the dominant axis. The same applies to the second projection 605, and the other projections (not illustrated). As shown, the dominant axis is assigned to the table entry corresponding to the second projection 605 because it is aligned with and in the direction of the force of gravity 607. In alternative embodiments, the dominant axis is assigned to the table entry corresponding to the projection that is aligned with and in the opposite direction of the force of gravity 607.

Tables may have any number of entries. Increasing the number of entries increases the number of projections that represent the probability range, and decrease the space swept by each projection. For example, in a table with twenty six entries, each entry could correspond to a projection having an included angle between opposite sides of forty five degrees.

Figure 7A:
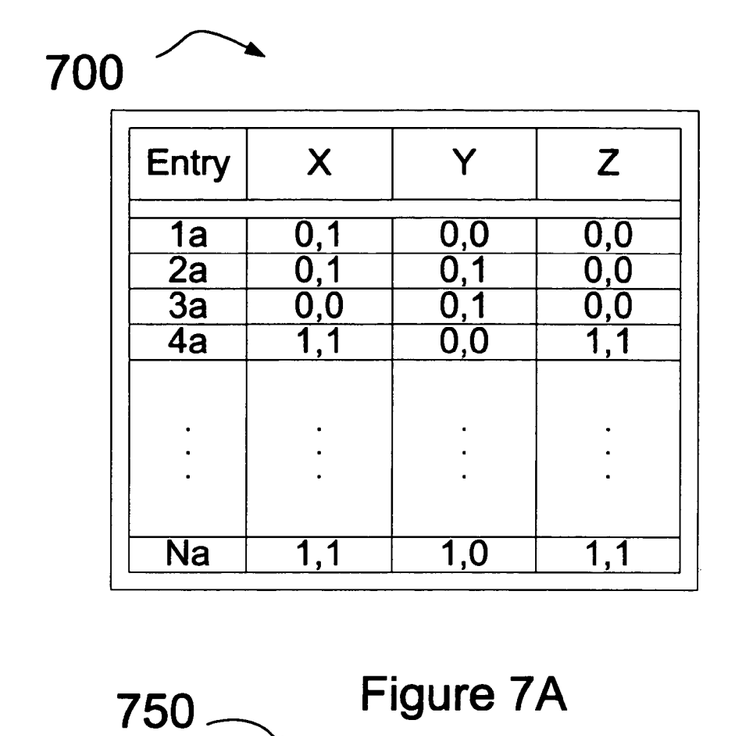
FIG. 7A illustrates an exemplary lookup table.

FIG. 7A illustrates an exemplary lookup table 700 having a plurality of entries, 1a, 2a, 3a, 4a through Na. Each entry has two binary numbers assigned to each of the x, y, and z axes. The first binary number represents whether gravity is acting in a negative or positive direction. The second binary number represents whether the magnitude of gravity exceeds a set threshold. In one embodiment, the threshold is set to about 38.4% of total gravitational influence. In alternative embodiments, thresholds with greater or lesser values are used. In one embodiment, the threshold may be preset based upon application or other criteria. Alternatively, the threshold may change during device operation, such as to adjust for a change in accuracy requirements.

The dominant axis is assigned to entry 1a when the x axis measures a negative average acceleration greater than the threshold, and neither the y-axis nor the z-axis measure an average acceleration value greater than the threshold. The dominant axis is assigned to entry 4a when the x-axis measures a positive average acceleration greater than the threshold, the y-axis measures an average acceleration value below the threshold, and the z-axis measures a positive average acceleration greater than the threshold. The dominant axis is assigned to entry Na when the x-axis measures a positive average acceleration greater than the threshold, the y-axis measures a negative average acceleration value above the threshold, and the z-axis measures a positive acceleration greater than the threshold. Where different gravitational influences are detected, the dominant axis is assigned to other entries.

Figure 7B:
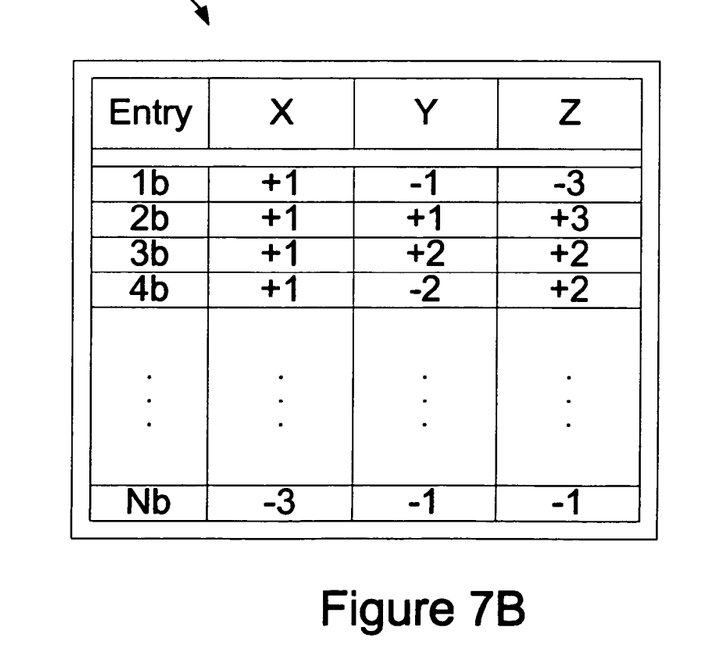
FIG. 7B illustrates an exemplary lookup table.

In alternative embodiments, multiple threshold values may be used based upon a range of average rolling acceleration values. FIG. 7B illustrates an exemplary lookup table 550 having a plurality of entries, 1b, 2b, 3b, 4b through Nb. Each entry can have a value of between −3 and 3, depending on what thresholds, if any, are met. In one embodiment, thresholds are set according to sine calculations made on the angles that will be swept by the projections represented by table entries. For example, in the exemplary lookup table of FIG. 7B, the acceleration range of 0-38.2% of total gravitational influence is assigned to threshold value 1, which is the sine of angles 0 degrees through 22.5 degrees. The acceleration range of 38.3%-92.3% is assigned to threshold value 2 (sine of angles 22.5 degrees through 67.5 degrees), and the acceleration range of 92.4% is assigned to threshold value 3 (sine of angles 67.5 degrees through 90 degrees). In alternative embodiments, different threshold values and/or number of thresholds are used. Different methods for setting threshold values can also be used. Each of the thresholds can have a positive or negative value.

In FIG. 7B, the dominant axis is assigned to entry 1b when the x-axis measures an average acceleration of about zero, the y-axis measures a positive average acceleration of 7.5% of total gravitational influence, and the z-axis measures a negative average acceleration of 92.5% of total gravitational influence. The dominant axis is assigned to entry 4b when the x-axis measures a positive average acceleration of 10% of total gravitational influence, the y-axis measures a negative average acceleration of 39% of total gravitational influence, and the z-axis measures a positive average acceleration of 51% of total gravitational influence. Where different gravitational influences are detected, the dominant axis is assigned to another entry.

In alternative embodiments, the dominant axis logic 110 assigns the dominant axis by using other data structures, for example, associative arrays, hash tables, adjacency matrices, etc. As with the lookup table, the accuracy of the other data structures is increased by using more entries.

Returning to FIG. 1, in one embodiment, the motion recognition logic 120 detects gestures and/or steps by utilizing data regarding the dominant axis. In one embodiment, certain gestures and/or steps are detected by utilizing the acceleration along only the dominant axis. In other embodiments, acceleration along other axes may also be used and/or acceleration along only the non-dominant axes may be used. In one embodiment, the dominant axis assignment is used to determine whether a step and/or gesture recognition cycle should be started. In one embodiment, certain gestures may only be detected when the dominant axis corresponds to a particular axis when the gesture is started. After the certain gestures have begun, assignment of the dominant axis may be unimportant to continue the gesture recognition.

Figure 8:
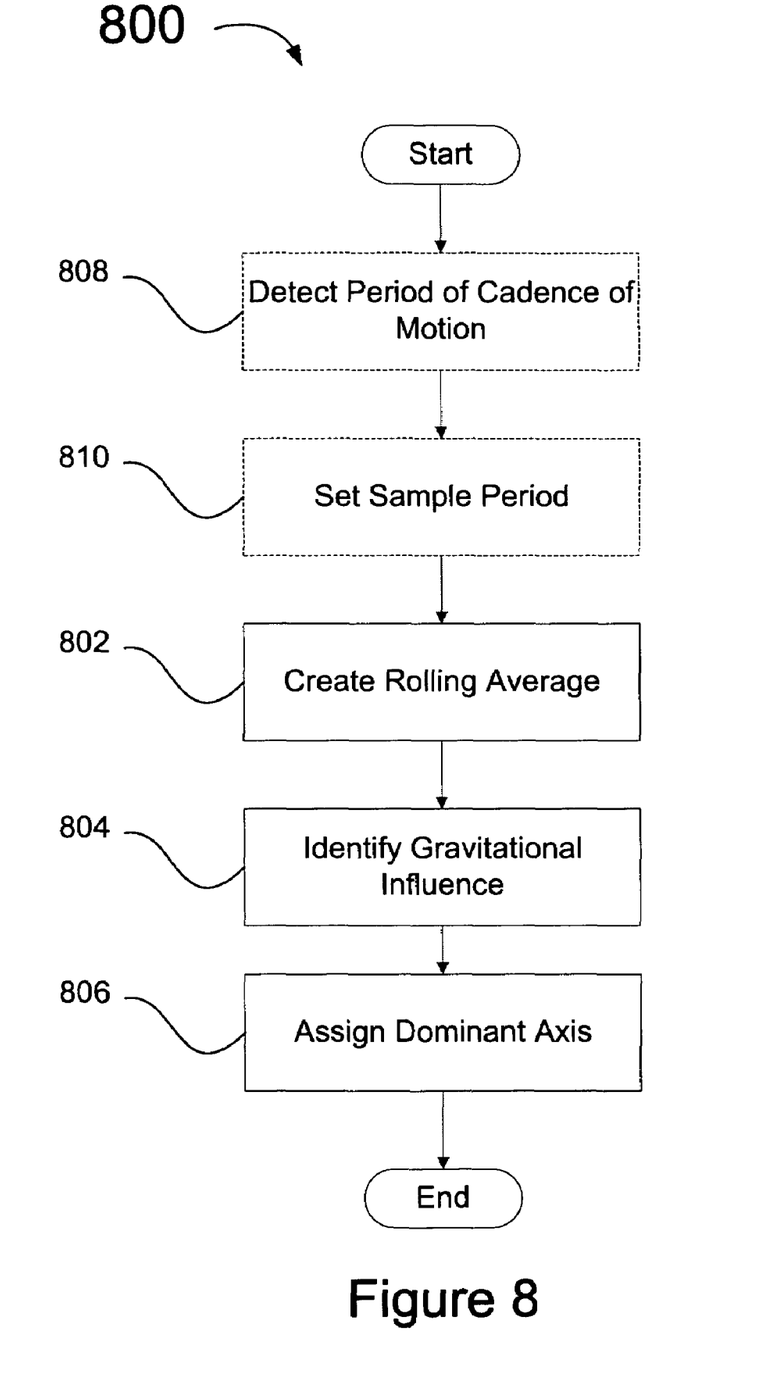
FIG. 8 shows a processing diagram for a method of determining an orientation of an accelerometer in accordance with one embodiment of the present invention.

FIG. 8 shows a processing diagram 800 for a method of determining an orientation of an accelerometer, in accordance with one embodiment of the present invention. In one embodiment, determining an orientation of the accelerometer determines an orientation of a device that includes the accelerometer.

At processing block 802, one or more rolling averages of accelerations are created over a sample period. The rolling averages can be simple rolling averages or weighted rolling averages such as exponential rolling averages. In an exponential rolling average, recent data is weighed more heavily relative to old data. The weighting applied to the most recent price depends on the specified period of the rolling average. The shorter the period, the more weight that will be applied to the most recent measurement. This can cause the rolling average to react more quickly to changing conditions.

The sample period over which the rolling averages are created can be pre-configured, adjusted based upon applications being used, user selected, or determined dynamically. In one embodiment, two or more rolling averages of accelerations are created concurrently along the same axes. The concurrent rolling averages can have different sample periods.

In one embodiment, if the sample period over which creation of the rolling averages of accelerations is determined dynamically, a period of a cadence of motion is detected at processing block 808. Subsequently, a sample period is set at processing block 810 based upon the period of the cadence of motion. In one embodiment, the sample period is set such that it has at least the period of the cadence of motion. In one embodiment, the sample period is set to a multiple of the period of the cadence of motion. In one embodiment, periods can be determined for multiple cadences of motions at processing block 808, and sample periods can be set for each determined cadence of motion. This embodiment facilitates the concurrent creation of two or more rolling averages of accelerations over different sample periods.

In one embodiment, the orientation of the accelerometer is determined based upon the rolling average or averages of accelerations. In one embodiment, determining the orientation of the accelerometer further includes identifying a gravitational influence based on the rolling averages of accelerations and determining the orientation, compared to the X-Y-Z axes of the accelerometer.

At processing block 804, a gravitational influence is identified based upon the rolling average of accelerations. In one embodiment, the gravitational influence is identified by calculating the total acceleration based upon the acceleration on each axis. In such an embodiment, a percentage of the total acceleration can then be assigned to each axis and an approximate device orientation can be determined. At processing block 806, a dominant axis is assigned based upon the gravitational influence.

In one embodiment, data regarding the dominant axis is utilized to detect a gesture, step, and/or motion. In one embodiment, acceleration along only the dominant axis is utilized. In another embodiment, acceleration along other axes may also be used.

In the foregoing description, numerous specific details have been set forth such as examples of specific systems, languages, components, etc. in order to provide a thorough understanding of the present invention. It will be apparent, however, to one skilled in the art that these specific details need not be employed to practice the present invention. In other instances, well known materials or methods have not been described in detail in order to avoid unnecessarily obscuring the present invention.

The present invention may be performed by hardware components or may be embodied in machine-executable instructions, which may be used to cause a general-purpose or special-purpose processor programmed with the instructions to perform the method described above. Alternatively, the method may be performed by a combination of hardware and software.

The present invention may be provided as a computer program product, or software, that may include a machine-readable medium having stored thereon instructions, which may be used to program a computer system (or other electronic devices) to perform a process according to the present invention. The machine-readable medium may include, but is not limited to, floppy diskettes, optical disks, CD-ROMs, and magneto-optical disks, ROMs, RAMs, EPROMs, EEPROMs, magnetic or optical cards, flash memory, or other type of media or machine-readable mediums suitable for storing electronic instructions.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method of determining an orientation of an accelerometer, comprising:
   creating one or more rolling averages of accelerations over a sample period;
   identifying a gravitational influence based upon the one or more rolling averages of accelerations; and
   assigning a dominant axis based upon the gravitational influence, wherein assigning the dominant axis comprises identifying an axis that has a largest average acceleration over the sample period.

2. The method of claim 1, wherein the dominant axis does not correspond to one of the actual axes of the accelerometer in its current orientation.

3. The method of claim 1, comprising:
   detecting a period of a cadence of motion; and
   setting the sample period such that it has at least the period of the cadence of motion.

4. The method of claim 3, comprising:
   setting the sample period to a multiple of the period of the cadence of motion.

5. The method of claim 1, comprising:
   utilizing acceleration along the dominant axis to detect a gesture, a periodic human motion, or a gesture and a periodic human motion.

6. The method of claim 5, comprising:
   utilizing acceleration along only the dominant axis.

7. The method of claim 1, comprising:
   creating a rolling average of accelerations over a sample period for each axis of the accelerometer; and
   identifying a gravitational influence based upon the rolling averages of accelerations by comparing the rolling average of accelerations of each axis of the accelerometer.

8. The method of claim 1, wherein the orientation is determined to a specified degree of accuracy.

9. A method of determining an orientation of an accelerometer, comprising:
   creating one or more rolling averages of accelerations over a sample period;
   identifying a gravitational influence based upon the one or more rolling averages of accelerations;
   comparing the gravitational influence to a lookup table; and
   assigning the dominant axis based upon the gravitational influence and the lookup table.

10. The method of claim 9, wherein the lookup table includes a plurality of entries, each entry defining a probability range for a distinct orientation for the gravitational influence.

11. The method of claim 9, wherein the lookup table divides accelerations into limits that define probability ranges in which gravity is acting, each entry in the lookup table being associated with a distinct probability range.

12. The method of claim 9, wherein each entry in the lookup table includes a gravity threshold for an axis of the accelerometer, the gravity threshold identifying a percentage of a total gravity caused acceleration.

13. A device, comprising:
a rolling average logic to create one or more rolling averages of accelerations as measured by an accelerometer over a sample period;
a gravitational influence logic to identify a gravitational influence based upon the one or more rolling averages of accelerations; and
a dominant axis logic to assign a dominant axis based upon the gravitational influence, wherein the dominant axis is an axis that has a largest average acceleration over the sample period.

14. The device of claim 13, wherein the dominant axis does not correspond to one of the actual axes of the accelerometer in its current orientation.

15. The device of claim 13, comprising:
a cadence logic to detect a period of a cadence of motion; and
a sample period logic to set the sample period such that it has at least the period of the cadence of motion.

16. The device of claim 15, wherein the sample period logic sets the sample period to a multiple of the period of the cadence of motion.

17. The device of claim 13, comprising:
a motion recognition logic to utilize acceleration along the dominant axis to detect a gesture, a periodic human motion, or a gesture and a periodic human motion.

18. The device of claim 17, wherein the motion recognition logic utilizes acceleration along only the dominant axis.

19. The device of claim 13, wherein the one or more rolling average of accelerations include a different rolling average of accelerations for each axis of the accelerometer, and wherein the gravitational influence logic is configured to identify the gravitational influence by comparing the rolling average of accelerations of each axis of the accelerometer.

20. A device, comprising:
a rolling average logic to create one or more rolling averages of accelerations as measured by an accelerometer over a sample period;
a gravitational influence logic to identify a gravitational influence based upon the one or more rolling averages of accelerations;
a dominant axis logic to assign a dominant axis based upon the gravitational influence; and
a lookup table, wherein the dominant axis logic uses the lookup table to assign a dominant axis based upon the gravitational influence.

21. The device of claim 20, wherein the lookup table includes a plurality of entries, each entry defining a probability range for a distinct orientation for the gravitational influence.

22. The device of claim 20, wherein the lookup table divides accelerations into limits that define probability ranges in which gravity is acting, each entry in the lookup table being associated with a distinct probability range.

23. The device of claim 20, wherein each entry in the lookup table includes a gravity threshold for an axis of the accelerometer, the gravity threshold identifying a percentage of a total gravity caused acceleration.

24. A portable electronic device, comprising:
an accelerometer having a plurality of axes;
a rolling average logic to create a rolling average of accelerations for each of the plurality of axes as measured by the accelerometer over a sample period;
a gravitational influence logic to identify a gravitational influence based upon rolling averages of accelerations by comparing the rolling average of accelerations of each of the plurality of axes; and
a dominant axis logic to assign a dominant axis based upon the gravitational influence.

25. The portable electronic device of claim 24, comprising:
a cadence logic to detect a period of a cadence of motion; and
a sample period logic to set the sample period such that it has at least the period of the cadence of motion.

26. The portable electronic device of claim 24, comprising:
a motion recognition logic to utilize acceleration along the dominant axis to detect a gesture, a periodic human motion, or a gesture and a periodic human motion.

27. The portable electronic device of claim 26, wherein the motion recognition logic utilizes acceleration along only the dominant axis.

28. A machine-accessible medium including data that, when accessed by a machine, cause the machine to perform a method comprising:
creating one or more rolling averages of accelerations over a sample period;
identifying a gravitational influence based upon the one or more rolling averages of accelerations; and
assigning a dominant axis based upon the gravitational influence, wherein assigning a dominant axis comprises identifying an axis that has a largest average acceleration over the sample period.

29. The machine-accessible medium of claim 28, the method further comprising:
utilizing acceleration along the dominant axis to detect a gesture, a periodic human motion, or a gesture and a periodic human motion.

30. The machine-accessible medium of claim 28, the method further comprising:
detecting a period of a cadence of motion; and
setting the sample period such that it has at least the period of the cadence of motion.

31. A method of determining a device orientation comprising:
creating a rolling average of accelerations over a sample period for each axis of an accelerometer; and
determining an orientation of the accelerometer based upon the rolling average of accelerations by comparing the relative rolling average of accelerations of each axis of the accelerometer.

32. The method of claim 31, comprising:
detecting a period of a cadence of motion; and
setting sample periods for the rolling averages of accelerations such that they have at least the period of the cadence of motion.

33. The method of claim 31, comprising:
utilizing the orientation of the accelerometer to detect gestures, periodic human motions, or gestures and periodic human motions.

34. The method of claim 31, wherein the orientation of the accelerometer is determined to a specified degree of accuracy.

35. The method of claim 31, further comprising:
when a rolling average of accelerations changes, determining a new orientation of the accelerometer based upon the new rolling average of accelerations.

36. The method of claim 31, wherein determining the orientation of the accelerometer comprises:
calculating a total gravity caused acceleration based upon the rolling average of accelerations of each axis of the accelerometer;

assigning a percentage of the total gravity caused accelerations to each axis; and calculating the orientation of the accelerometer based on the percentage of the total gravity caused acceleration assigned to each axis.

37. A method of determining a device orientation comprising:

creating at least one rolling average of accelerations;

comparing the at least one rolling average of accelerations to a lookup table; and determining an orientation of the accelerometer based upon the at least one rolling average of accelerations and the lookup table.

38. A machine-accessible medium including data that, when accessed by a machine, cause the machine to perform a method comprising:

creating one or more rolling averages of accelerations over a sample period;

identifying a gravitational influence based upon the one or more rolling averages of accelerations;

comparing the gravitational influence to a lookup table; and assigning the dominant axis based upon the gravitational influence and the lookup table.

39. The machine accessible medium of claim 38, wherein the lookup table includes a plurality of entries, each entry defining a probability range for a distinct orientation for the gravitational influence.

40. The machine-accessible medium of claim 38, wherein the lookup table divides accelerations into limits that define probability ranges in which gravity is acting, each entry in the lookup table being associated with a distinct probability range.

41. The machine-accessible medium of claim 38, wherein each entry in the lookup table includes a gravity threshold for an axis of the accelerometer, the gravity threshold identifying a percentage of a total gravity caused acceleration.

42. A machine-accessible medium including data that, when accessed by a machine, cause the machine to perform a method comprising:

creating a rolling average of accelerations over a sample period for each axis of an accelerometer;

identifying a gravitational influence based upon the rolling averages of accelerations by comparing the rolling average of accelerations of each axis of the accelerometer; and assigning a dominant axis based upon the gravitational influence.

43. The machine-accessible medium of claim 42, the method further comprising:

assigning a new dominant axis based upon the rolling average of accelerations when the gravitational influence changes.

* * * * *